United States Patent [19]

Pellico

[11] 4,291,025

[45] Sep. 22, 1981

[54] AGAR GEL TOPICAL DRESSING

[75] Inventor: Michael A. Pellico, Los Angeles, Calif.

[73] Assignee: Laclede Professional Products, Inc., Brooklyn, N.Y.

[21] Appl. No.: 139,500

[22] Filed: Apr. 11, 1980

[51] Int. Cl.³ .................. A01N 31/00; A61K 31/70
[52] U.S. Cl. ................................... 424/180; 424/339; 424/342; 424/DIG. 13; 424/148; 424/361; 252/316
[58] Field of Search .................. 536/1, 122; 424/180, 424/361, DIG. 13, 127, 148, 343, 339, 342; 252/316

[56] References Cited

U.S. PATENT DOCUMENTS 4,112,121  9/1978  Tenta ..................... 424/DIG. 13
4,186,190  1/1980  Gregory .................. 424/DIG. 13

Primary Examiner—Delbert R. Phillips
Assistant Examiner—Blondel Hazel
Attorney, Agent, or Firm—Donald Diamond

[57] ABSTRACT

An agar gel topical dressing for coating a burn area or other area of skin impairment is prepared by heating and agitating a mixture of agar, diethylene glycol and water to solubilize the agar. The resulting solution, upon cooling to its gelation temperature, is converted to a thermally reversible agar gel. Application of the agar gel as a burn coating is undertaken by heating the gel to obtain a sol, applying the sol to the burn area at a tissue compatible temperature, and allowing the sol to cool and set in the form of a gel.

13 Claims, No Drawings

AGAR GEL TOPICAL DRESSING

BACKGROUND OF THE INVENTION

This invention relates to agar gel compositions, a method for making such compositions and a method for applying such compositions as topical dressings to a burn area or other area of skin impairment.

A burn is generally defined as a bodily injury or lesion caused by contact with, or exposure to, heat, chemicals, electricity or radiation. The burning agent, which changes or even destroys the affected tissue, injures and destroys cells by altering the protein component of such cells. In mild burns, there is cellular disorganization in the affected area; while in more severe burns, there is heat coagulation and charring with tissue necrosis.

Burns are customarily defined and classified according to (a) their degree as determined by their depth and the nature of the tissue involved, (b) their extent as determined by the area or percentage of body surface involved, and (c) the nature of the burning agent.

In first-degree burns, which are the least serious, damage is confined to the outer skin layers, or epidermis. Tissue cells, while affected, are generally not destroyed.

Second-degree burns involve the destruction of the epidermis and the upper layers of the dermis (superficial second-degree burns) or all but the deepest layers of the dermis (deep second-degree burns). In second-degree burns, islets of epithelium are left intact, particularly around undestroyed hair follicles and sweat glands. From these islets, there may be spontaneous regeneration of tissue, although healing is slow, and the deeper the burn the slower the healing. In addition, trauma, infection or other causes may impair tissue regeneration and result in full-thickness destruction of the skin. Since second-degree burns uncover nerve endings, the burned areas can be very painful, even from exposure to air.

Third-degree burns are those in which the full thickness of the skin (epidermis and dermis) is destroyed. Since sweat glands and hair follicles are likely to be destroyed, spontaneous regeneration of skin must usually be from the wound edge and, unless the burned area is small and localized, skin grafting is necessary to prevent scarring and to restore function.

Burns may also be classified as fourth-degree and char burns. When the full thickness of the skin and tissue beneath the skin have been destroyed, the burn may be called fourth-degree. A burn may be called a char burn when a body area is destroyed by charring which leaves a black appearance.

In the management of burns, therapeutic coatings and dressings are employed to keep the wound clean, to act as a barrier against external contamination, to suppress bacterial growth at the wound site, to promote healing and reepitheliazation in second-degree or partial thickness burns and to promote the formation of satisfactory granulations tissue in third-degree or full thickness burns as a base for skin grafting.

The therapeutic coatings and dressings may be employed in the form of spreadable and film forming compositions and in the form of impregnated gauze and bandages. The coatings and dressings may be formulated with potent antibacterials such as nitrofurazone or silver sulfadiazine.

It is disclosed in the art that a soluble dressing containing nitrofurazone in a water-soluble base of polyethylene glycols may be applied directly to the lesion or that a gauze or bandage impregnated with the dressing can be used; that a solution containing nitrofurazone dissolves in a water-miscible liquid of polyethylene glycol and water may be sprayed on painful lesions or burns and, upon evaporation of the water, a transparent film of nitrofurazone and polyethylene glycol remains; and that a topical cream containing nitrofurazone in a water-miscible base consisting of glycerin, cetyl alcohol, mineral oil, and ethoxylated fatty alcohol, methylparaben, propylparaben and water may be applied directly to the lesion or that gauze impregnated with the cream can be used. It is also disclosed in the art that a water-miscible cream containing silver sulfadiazine in a vehicle consisting of white petrolatum, stearyl alcohol, isopropyl myristate, sorbitan monooleate, polyoxyl 40 stearate, propylene glycol, methyl paraben and water may be applied to the burn wound as an adjunct for the prevention and treatment of wound sepsis in patients with second- and third-degree burns.

SUMMARY OF THE INVENTION

In one aspect of this invention, there is provided a thermally reversible agar gel topical dressing for coating a burn area or other area of skin impairment which comprises about 5 to about 12 wt.% agar, about 20 to about 75 wt.% diethylene glycol and water to 100 wt.%.

In a second aspect of this invention, there is provided a method for preparing a thermally reversible agar gel topical dressing having a gelation temperature from about 24 to about 49° C., which comprises heating and agitating a mixture containing about 5 to about 12 wt.% agar, about 20 to about 75 wt.% diethylene glycol and water to 100 wt.% to solubilize the agar and allowing the resulting solution to cool and set in the form of a thermally reversible gel.

In a third aspect of this invention, there is provided a method for applying a thermally reversible agar gel as a topical dressing to a burn area or other area of skin impairment, which comprises (a) heating an agar gel containing about 5 to about 12 wt.% agar, about 20 to about 75 wt.% diethylene glycol and water to 100 wt.% to obtain a sol; (b) applying the sol at a tissue compatible temperature to the burn area or other area of skin impairment; and (c) allowing the sol to cool and set in the form of a gel.

DETAILED DESCRIPTION

A. Composition

Agar is the dried mucilagenous substance extracted from plants found growing chiefly off the coasts of Japan, China, Ceylon, Malaya and Southern California. These plants are of the species Gelidium, in particular *Gelidium corneum*, and other closely related algae (class Rhodophyceae). The final product is obtained through drying and grinding of the plants, yielding in most cases a medium-sized mesh powder.

Chemically, agar is the sulfuric acid ester of a linear galactan, a polysaccharide. Hydrolysis yields the hexose sugars D-galactose and L-galactose, and sulfuric acid in a constant 9:1:1 ratio. In addition, there are several cations associated with the composition, with the principal cation being calcium. These cations are believed to be the cross-linking agents in thick solutions of agar and their subsequent gels. The average chain length of this polysaccharide is anywhere from 200 to 250 sugar residues in length, depending upon the species from which it was originally extracted. Agar is insoluble in cold water, but is slowly soluble in hot water to give a viscous, straw colored solution. A 1% agar solution melts at 80° to 100° C. and sets at 35° to 50° C. to a rigid gel.

The agar which is most suitable for use in the compositions of this invention has a bloom strength from at least about 600 up to about 800 or more. The term "bloom strength" identifies the gel strength of an agar gel prepared by dissolving one gram of pure agar in 99 grams of boiling water, cooling the agar solution to form a gel and applying a penetrometer to the gel to measure gel or bloom strength.

In order to produce thermally reversible agar gels which are suitable for use as burn coatings, the gels should contain from about 5 to about 12 wt.% agar and have a gelation or set temperature below about 49° C. so that the gel precursor, namely, the agar sol, can be applied to a burn area at a tissue compatible temperature. However, an aqueous agar gel containing 5 wt.% agar has a gelation temperature of about 51.7° C., while an aqueous agar gel containing 10 wt.% agar has a gelation temperature of about 54.4° C. Thus, thermally reversible aqueous agar gels containing from about 5 to about 12 st.% agar are not particularly well suited for use as burn coatings because their gelation temperatures require application of the agar sol to a burn wound at a temperature which is above tissue compatible temperature.

In accordance with this invention, it has been discovered that the gelation temperature of thermally reversible aqueous agar gels can be reduced below about 49° C. by including diethylene glycol in the gel formulation. This beneficial result, which permits the corresponding agar sol to be applied to a burn area at a tissue compatible temperature, is attained when diethylene glycol is present in the gel formulation in an amount from about 20 to about 75 wt.% and, preferably, in an amount from about 40 to about 55 wt.%. The gelation temperature of the agar/diethylene glycol/water thermally reversible gel can be selectively reduced from about 49° to about 24° C. by increasing the concentration of the diethylene glycol within the range from about 20 to about 75 wt.% until the desired gelation temperature is obtained. This significant lowering of the gelation temperature of aqueous agar gels is not attained when other polyol alcohols such as dipropylene glycol, propylene glycol or ethylene glycol are substituted for diethylene glycol in the gel formulation. In addition to lowering the gelation temperature of agar gels, diethylene glycol also functions as a plasticiser to impart high strength yieldability to the gel and as a humectant to assist the gel dressing in absorbing fluids from the burn wound. It is also believed that the diethylene glycol makes a significant contribution to the antibacterial properties and characteristics exhibited by the gel compositions of this invention.

As an adjunct to the aforesaid ingredients, gel strengthening agents, which impart added toughness to the gel dressings, may advantageously be included in the gel formulations in an amount from about 0.1 to about 2 wt.%. Certain multivalent salts have been found to be particularly effective as agents for increasing the toughness of the gel dressings. These salts include borates and sulfates such as sodium borate, potassium borate, potassium sulfate and zinc sulfate.

The gel dressings of this invention may be further formulated with special purpose ingredients such as vitamins, amino acids, antibiotics, antibacterials, topical sedatives, humectants, and skin penetrating oils in suitable concentrations and which are compatible with the gel dressings described herein.

B. Method Of Preparation

The termally reversible, agar gel topical dressings, which have a gelation temperature from about 24° to about 49° C. are prepared by heating and agitating an admixture containing agar, diethylene glycol and water to solubilize the agar and allowing the resulting agar solution to cool and set in the form of a gel. The admixture comprises about 5 to about 12 wt.% agar, about 20 to about 75 wt.% diethylene glycol and water to 100 wt.%. In a narrower aspect, the admixture contains from about 8 to about 10 wt.% agar and from about 40 to about 55 wt.% diethylene glycol.

The admixture is advantageously heated and agitated at a temperature from about 90° to about 140° C. for a sufficient length of time, usually from about one to two hours for relatively small batches, to effect complete solubilization of the powdered agar in the diethylene glycol/water fluid medium. Solubilization of the agar in the fluid medium may be carried out in any suitable apparatus as, for example, an open or closed steamjacketed kettle equipped with an appropriate stirrer. When a special purpose ingredient such as a gel strengthening agent is to be included in the gel formulation, it is advantageously added to the admixture after the agar has been substantially dissolved but prior to the completion of the heating and agitation step.

Following the solubilization step, the resulting hot agar solution or sol may be transferred to a suitable container and allowed to cool. The agar sol, upon reaching its gelation temperature, sets in the form of a high strength gel which may be ground or chopped into small pellets or pieces to facilitate subsequent melting and liquification for spreadable application and reset as a topical gel dressing.

C. Method Of Use

The termally reversible, agar gel topical dressing containing agar, diethylene glycol and water in the proportions herein specified is employed as a topical coating for a burn area or other area of skin impairment by a procedure, which comprises: heating the gel to a sufficient temperature to melt and liquify the gel and convert it to a sol; (b) applying the sol at a tissue compatible temperature to the burn area or other area of skin impairment and (c) allowing the sol to cool and reset in the form of a gel.

The gel is advantageously converted to a sol by heating and agitating gel pieces or pellets in a stirrer equipped vessel at a temperature from about 88° to about 93° C. or higher for a sufficient length of time to completely liquify the gel. In this temperature range, conversion of a relatively small gel batch to a sol is usually effected within about 15 minutes.

The agar sol, which is in the form of a highly viscous fluid, retains its fluidity until it reaches its gelation temperature. As hereinabove pointed out, the agar gel dressings of this invention are selectively formulated with diethylene glycol so as to have a gelation temperature between about 24° and about 49° C. The agar sol is advantageously maintained and applied to the burn wound at a temperature which is a few degrees above its gelation temperature, but not in excess of tissue compatible temperature. Upon cooling, the viscous agar sol resets in the form of a high strength gel dressing. In order to maintain the gel in a substantially fixed, tissue abutting relationship at the burn site, it is advantageous to secure a wide mesh cloth grid across the burn area and apply the agar sol to the grid which acts as a situs support for the resulting gel. As more particularly shown in a subsequent example, it has been observed that the agar gel topical dressings of this invention promote the healing of partial thickness burns and exhibit antibacterial properties and characteristics.

EXAMPLES

The following examples further illustrate the agar gel topical dressings of this invention. The agar used in the examples was a high gel strength agar having a bloom strength in excess of 600 with a one cubic inch sample of agar gel being resistant to indentation upon being loaded with a weight force between 400 and 800 grams.

EXAMPLE I

This example contrasts the effects of diethylene glycol and dipropylene glycol as additives for lowering the gelation temperature of thermally reversible, aqueous agar gels. The agar gel compositions were prepared by heating an admixture of the gel ingredients with agitation to a temperature of 100° C. and maintaining the admixture at this temperature with continued agitation until the agar was completely solubilized. Following the solubilization step, the resulting solutions or sols were allowed to cool under ambient conditions and the gelation temperatures were determined. The formulations for the small batch runs and their gelation temperatures are set forth in the following table:

TABLE I

| Ingredients | Run No. | | | |
|---|---|---|---|---|
| | 1 | 2 | 3 | 4 |
| Agar, wt. % | 5 | 5 | 5 | 5 |
| Water, wt. % | 95 | 45 | 45 | 80 |
| Diethylene glycol, wt. % | — | — | 50 | 20 |
| Dipropylene glycol, wt. % | — | 50 | — | — |
| Gelation temp. °C. | 51.7 | 51.7 | 40.6 | 45.7 |

As shown in the foregoing table, a 5% aqueous agar gel (Run No. 1) has a gelation temperature of 51.7° C. The formulation of a 5% agar gel with 45% water and 50% dipropylene glycol (Run No. 2) had no effect on gelation temperature in that the gelation temperature, at 51.7° C, was the same as the gelation temperature of the 5% aqueous agar gel of Run No. 1. In contrast thereto, the formulation of a 5% agar gel with 45% water and 50% diethylene glycol (Run No. 3) produced a sol which had a gelation temperature of 40.6° C.

EXAMPLE II

This example illustrates the effect on the gelation temperature of aqueous agar gels formulated with increasing concentrations of diethylene glycol. The agar gel compositions were prepared and allowed to cool and set to a gel in accordance with the procedure described in Example I. The formulations for the small batch runs and their gelation temperatures are set forth in the following table:

TABLE II

| Ingredients | Run No. | | | |
|---|---|---|---|---|
| | 1 | 2 | 3 | 4 |
| Agar, wt. % | 10 | 10 | 10 | 10 |
| Water, wt. % | 90 | 70 | 60 | 30 |
| Diethylene glycol, wt. % | — | 20 | 30 | 60 |
| Gelation temp. °C. | 54.4 | 49 | 46 | 24 |

As shown in Table II, a 10% aqueous agar gel (Run No. 1) has a gelation temperature of 54.4° C; a 10% agar gel formulated with 70% water and 20% diethylene glycol (Run No. 2) has a gelation temperature of 49° C; a 10% agar gel formulated with 60% water and 30% diethylene glycol has a gelation temperature of 46° C; and a 10% agar gel formulated with 30% water and 60% diethylene glycol has a gelation temperature of 24° C. Thus, from the data set forth in Table II, it will be noted that the gelation temperature of the agar/water/diethylene glycol system is inversely proportional to the concentration of diethylene glycol in the system.

EXAMPLE III

This example shows the effect of the agar gel compositions of this invention on (a) the rate of healing and (b) bacterial growth when the gel is applied to a partial thickness burn as a topical dressing.

The thermally reversible, agar gel employed in this example had the following formulation:

| Ingredients | Wt. % |
|---|---|
| Agar | 8.000 |
| Water | 36.875 |
| Diethylene glycol | 55.000 |
| Sodium borate | 0.125 |
| | 100.000 |

The agar gel (3.64 kg) was prepared by heating and agitating an admixture of agar, water and diethylene glycol for about two hours at about 100° C, with sodium borate being added to the admixture at about the halfway point in the heating cycle. Following the heating step in which the agar and sodium borate were solubilized in the water/diethylene glycol fluid medium, the resulting sol, upon cooling under ambient conditions, solidified in the form of a high strength, yieldable gel. The agar gel, which had a gelation temperature of about 37.5° C, was subdivided into small pieces.

A comparative study of this agar gel as a burn coating for partial thickness burns was undertaken by a medical research group at a burn center.

Eight Spraque-Dowley rats, after being anesthetized with 40 mg/kg ketamine and 100 mg/kg sodium pentobarbital, were given partial thickness burns over 20% of their body surface area (dorsal) using a scald technique with 90° C. water for five minutes.

The agar gel was prepared for use as a burn coating by heating and agitating the small gel pieces at a temperature above 88° C. to convert the gel to a sol. The sol, which had a gelation temperature of about 37.5° C, was cooled to and maintained at a temperature of about 39.5° C. in the form of a highly viscous fluid.

In the comparative study, four rats were treated with the agar sol/gel, one rat was treated with silver sulfadiazine ointment and three rats were untreated. Treatment with the agar sol, which was applied to the burn areas of four rats at a temperature of about 39.5° C, was begun within one hour post burn and then applied once daily thereafter throughout a 34 day study. The sol solidified into a removable gel form within a few minutes following application to the burn site.

Bacteriologies of the burn areas were taken on the 14th day. Small biopsies were ground in 5 ml of media and then plated on blood agar which was incubated at 37° C. for 24 hours. Bacteria counts, which were recorded as colonies per gram tissue, are set forth in Table III:

TABLE III

| Rat No. | Bacteria Count, Colonies/Gram Tissue | | |
|---|---|---|---|
| | Agar Gel | Silver Sulfadiazine | Untreated |
| 1 | $4.3 \times 10^6$ | | |
| 2 | $4.1 \times 10^6$ | | |
| 3 | $4.6 \times 10^6$ | | |
| 4 | $20.7 \times 10^6$ | | |
| 5 | | $4.8 \times 10^5$ | |
| 6 | | | $18.8 \times 10^8$ |
| 7 | | | $6.7 \times 10^8$ |
| Average | $8.4 \times 10^6$ | $4.8 \times 10^5$ | $12.8 \times 10^8$ |

The time to complete healing was judged as the time required to complete 100% reepithelialzation of the partial thickness burn areas. For the rats treated with the agar composition, the average healing time was 23.9 days; for the rat treated with silver sulfadiazine, the healing time was 21 days; and for the untreated rats the average healing time was 35.6 days.

Weights were taken for the untreated and gel treated rats during the 34 day study. Rats in both groups initially lost weight. However, the gel treated rats during the latter part of the study began an upward weight climb which extended beyond their pre-burn weight while the untreated rats exhibited a cyclic weight pattern below the pre-burn weight.

One control rat died on day 22 after becoming noticeably sick by day 16 and one mortality occurred from anesthesia.

As shown by the foregoing study, the agar gel compositions of this invention, when employed as a topical dressing for partial thickness burn wounds, increase the rate of healing of the wound and impede bacterial growth at the would site.

In view of the foregoing description and examples, it will become apparent to those of ordinary skill in the art that equivalent modifications thereof may be made without departing from the spirit and scope of this invention.

That which is claimed is:

1. An agar gel topical dressing, which comprises about 5 to about 12 wt.% agar, about 20 to about 75 wt.% diethylene glycol and water to 100 wt.%.

2. The dressing of claim 1 wherein the concentration of agar is from about 8 to about 10 wt.% and the concentration of diethylene glycol is from about 40 to about 55 wt.%.

3. The dressing of claim 1 which includes a gel strengthening agent selected from the group consisting of sodium borate, potassium borate, potassium sulfate, zinc sulfate and mixtures thereof.

4. A method for preparing a thermally reversible, agar gel topical dressing having a gelation temperature from about 24° to abour 49° C, which comprises heating and agitating an admixture containing about 5 to about 12 wt.% agar, about 20 to about 75 wt.% diethylene glycol and water to 100 wt.% to solubilize the agar and allowing the resulting solution to cool and set in the form of a gel.

5. The method of claim 4 wherein the admixture contains from about 8 to about 10 wt.% agar and from about 40 to about 55 wt.% diethylene glycol.

6. The method of claim 4 wherein the admixture includes a gel strengthening agent selected from the group consisting of sodium borate, potassium borate, potassium sulfate, zinc sulfate and mixtures thereof.

7. The method of claim 4 wherein the mixture is heated and agitated at a temperature between about 90° and about 104° C. to solubilize the agar.

8. A method for applying an agar gel topical dressing to a burn area or other area of skin impairment, which comprises:
 (a) heating a thermally reversible, agar gel topical dressing containing about 5 to about 12 wt.% agar, about 20 to about 75 wt.% diethylene glycol and water to 100 wt.% to obtain a sol, said sol having a gelation temperature from about 24° to about 49° C.;
 (b) applying the sol at a tissue compatible temperature to the burn area or other area of skin impairment; and
 (c) allowing the sol to cool and set in the form of a gel.

9. The method of claim 8 wherein the dressing contains from about 8 to about 10 wt.% agar and from about 40 to about 55 wt.% diethylene glycol.

10. The method of claim 8 wherein the agar gel topical dressing includes a gel strengthening agent selected from the group consisting of sodium borate, potassium borate, potassium sulfate, zinc sulfate and mixtures thereof.

11. The method of claim 8 wherein the agar gel topical dressing is heated to and maintained at a temperature from about 88° to about 93° C. to convert the topical dressing from a gel to a sol.

12. The method of claim 8 wherein the sol is applied to a wide mesh support grid overlying the burn area or other area of skin impairment.

13. The method of claim 8 wherein the sol is applied to the burn area or other area of skin impairment at a temperature above its gelation point and below about 51° C.

* * * * *